United States Patent
Pachmann et al.

(10) Patent No.: US 11,920,163 B2
(45) Date of Patent: Mar. 5, 2024

(54) METHOD FOR CULTURING A SUBPOPULATION OF CIRCULATING EPITHELIAL TUMOUR CELLS FROM A BODY FLUID

(71) Applicants: Ulrich Pachmann, Bayreuth (DE); Katharina Pachmann, Bayreuth (DE)

(72) Inventors: Ulrich Pachmann, Bayreuth (DE); Katharina Pachmann, Bayreuth (DE)

( * ) Notice: Subject to any disclaimer, the term of this patent is extended or adjusted under 35 U.S.C. 154(b) by 146 days.

(21) Appl. No.: 17/233,783

(22) Filed: Apr. 19, 2021

(65) Prior Publication Data

US 2021/0238554 A1 Aug. 5, 2021

Related U.S. Application Data

(62) Division of application No. 14/419,149, filed as application No. PCT/EP2013/066325 on Aug. 2, 2013, now Pat. No. 11,015,172.

(30) Foreign Application Priority Data

Aug. 3, 2012 (DE) .................. 10 2012 213 838

(51) Int. Cl.
| | | |
|---|---|---|
| C12N 5/09 | (2010.01) | |
| C12N 5/00 | (2006.01) | |
| C12N 5/095 | (2010.01) | |
| G01N 33/50 | (2006.01) | |

(52) U.S. Cl.
CPC ......... *C12N 5/0694* (2013.01); *C12N 5/0695* (2013.01); *G01N 33/5011* (2013.01); *C12N 5/0062* (2013.01); *C12N 2500/02* (2013.01); *C12N 2501/10* (2013.01); *C12N 2501/11* (2013.01); *C12N 2523/00* (2013.01); *G01N 2458/30* (2013.01)

(58) Field of Classification Search
CPC ............... C12N 5/0694; C12N 5/0062; C12N 2501/10; C12N 2501/11
See application file for complete search history.

(56) References Cited

U.S. PATENT DOCUMENTS

| | | |
|---|---|---|
| 2002/0076747 A1 | 6/2002 | Price et al. |
| 2006/0014157 A1 | 1/2006 | Kawabe et al. |
| 2010/0081200 A1 | 4/2010 | Rajala et al. |
| 2013/0078667 A1 | 3/2013 | Goodman et al. |
| 2014/0212895 A1 | 7/2014 | Lim |
| 2014/0322356 A1 | 10/2014 | Marchetti et al. |

FOREIGN PATENT DOCUMENTS

| | | |
|---|---|---|
| DE | 10 2009 047 146 A1 | 6/2011 |
| WO | WO 2007/079293 A2 | 7/2007 |

OTHER PUBLICATIONS

Chen et al., "Identification and expansion of cancer stem cells in tumor tissues and peripheral blood derived from gastric adenocarcinoma patients," Cell Research, 2012, vol. 22, pp. 248-258.
Chen et al., "Nonadhesive Culture System as a Model of Rapid Sphere Formation with Cancer Stem Cell Properties," PLoS One, Feb. 2012, vol. 7, Issue 2, pp. 1-11.
Dontu et al., "In vitro propagation and transcriptional profiling of human mammary stem/progenitor cells," Genes & Development, 2003, vol. 17, pp. 1253-1270.
Hekimian et al., Abstract of "Detection of tumor stem cells among circulating epithelial tumor cells (CETC) and relationship to therapy response," Cancer Research, Jan. 15, 2009, vol. 69, No. 2.
Hirschhaeuser et al., "Multicellular tumor spheroids: An underestimated tool is catching up again," Journal of Biotechnology, Jul. 1, 2010, vol. 148, No. 1, pp. 3-15.
International Search Report issued in PCT/EP2013/066325, dated Oct. 14, 2013.
Lu et al., "Isolation of circulating epithelial and tumor progenitor cells with an invasive phenotype from breast cancer patients," International Journal of Cancer, 2010, vol. 126, pp. 669-683.
Ueda et al., Aldehyde Dehydrogenase 1 Identifies Cells with Cancer Stem Cell-Like Properties in a Human Renal Cell Carcinoma Cell Line, PLOS One, Oct. 2013, vol. 8, Issue 10, pp. 1-10.
Wang et al., "Detection of circulating tumor cells and tumor stem cells in patients with breast cancer by using flow cytometry," A valuable tool for diagnosis and prognosis evaluation, Tumor Biology, Jan. 13, 2012, vol. 33, No. 2, pp. 561-569.
Allan et al., "Detection and Quantification of Circulating Tumor Cells in Mouse Models of Human Breast Cancer Using Immunomagnetic Enrichment and Multiparameter Flow Cytometry", Cytometry Part A, 65A:4-14 (Year: 2005).
Friedrich et al., "Spheriod-based drug screen: considerations and practical approach", Nature Protocols, vol. 4, No. 3, 2009, p. 309-324.
Marrinucci et al., "Circulating Tumor Cells From Well-Differentiated Lung Adenocarcinoma Retain Cytomorphologic Features of Primary Tumor Type", Arch Pathol Lab Med, 2009; 133:1468-1471 (Year: 2009).
Vinci et al., "Advances in establishment and analysis of three-dimensional tumour spheriod-based functional assays for target validation and drug evaluation", BMC Biology, 2012, 10:29, p. 1-20 (Year: 2012).
Wu, "Growth of Human Lung Tumor Cells in Culture", Culture of Human Tumor Cells, Edited by Roswitha Pfragner and R. Ian Freshney, p. 1-21 (Year 2004).

*Primary Examiner* — Taeyoon Kim
(74) *Attorney, Agent, or Firm* — Birch, Stewart, Kolasch & Birch, LLP

(57) ABSTRACT

The invention relates to a method for culturing a subpopulation of circulating epithelial tumour cells from a body fluid of a human or animal suffering from an epithelial tumour, wherein cells contained in the body fluid each containing at last one cell nucleus are separated from the body fluid and cultured over at least 24 hours in suspension, with formation of spheroids.

9 Claims, 2 Drawing Sheets

Figure 1A:
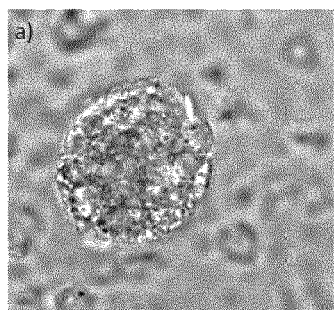

METHOD FOR CULTURING A SUBPOPULATION OF CIRCULATING EPITHELIAL TUMOUR CELLS FROM A BODY FLUID

This application is a Divisional of application Ser. No. 14/419,149 filed on May 29, 2015, which is the U.S. National Phase of PCT/EP2013/066325, filed Aug. 2, 2013, and which claims priority under 35 U.S.C. § 119(a) to Application No. 10 2012 213 838.2 filed in Germany, on Aug. 3, 2012, the entire contents of all of which are expressly incorporated by reference into the present application.

The invention relates to a method for culturing a subpopulation of circulating epithelial tumor cells from a body fluid from a human or animal. The animal can be a mammal.

Dontu, G. et al., Genes & Development 17, 2003, pages 1253 to 1270 disclose a method for in vitro culturing of human epithelial cells from breast tissue. The cells were generated by preparing single-cell suspensions of human mammary epithelial cells via mechanical and enzymatic dissociation of breast tissue and culturing said suspensions under conditions which do not allow adhesion to a substrate. In this method, only a small population of cells proliferated in suspension as so-called mammospheres.

Lu, J. et al., Int. J. Cancer 126, 2010, pages 669 to 683 disclose firstly enriching cells from peripheral blood from breast cancer patients by means of a Ficoll density gradient centrifugation and seeding the mononuclear cells thereby obtained on a collagen adhesion matrix and incubating them for 12 hours in a cell culture medium in a $CO_2$ cell incubator. Only cells able to adhere during this time are subsequently cultured further, whereas nonadherent cells and old medium are removed. The adherent cells are cultured by adding fresh cell culture medium, which is then replaced every 3 days with fresh cell culture medium. In this procedure, the number and size of cells increased over time in culture. After days, there were large spread cells with epithelial morphology.

DE 10 2009 047 146 A1 discloses a method for predicting the response of a solid epithelial tumor-induced tumor disease in a patient to a therapeutic measure. In said method, epithelial tumor cells from a body fluid from the patient are collected in a cell culture medium in each case. The cell culture medium preferably contains no added growth factor and no added growth factor-containing serum. Tumor cells from a sample of the tumor cell-containing cell culture medium are exposed to the therapeutic measure, whereas the tumor cells from an equal control sample of the tumor cell-containing cell culture medium remain untreated. Subsequently, for both the sample and the control sample, the proportion of dying and dead epithelial tumor cells with respect to the total number of epithelial tumor cells is determined and, from this, a therapeutic measure-related mortality rate for the epithelial tumor cells as a measure of the response. There may be a period of a few hours to days between the therapeutic measure and the determination of the proportion of dying and dead epithelial tumor cells with respect to the total number of epithelial tumor cells. During this period, the tumor cells are kept under customary cell culture conditions, which allow survival of the tumor cells in the cell culture medium in the absence of therapeutic measure. It is not disclosed that the tumor cells proliferate under these conditions.

It is an object of the present invention to provide an alternative method for culturing cells from a body fluid from patients suffering from a tumor disease attributable to an epithelial tumor. The cultured cells shall allow a characterization of the tumor disease. Furthermore, use of the cells cultured using said method and a therapeutic use of the tumor cells shall be provided.

The object is achieved by the features of the present invention as set forth herein. Useful embodiments of the present invention are also set forth herein.

The invention provides a method for culturing a subpopulation of circulating epithelial tumor cells from a body fluid from a human or animal, more particularly a mammal, affected by an epithelial tumor. In said method, cells present in the body fluid and containing at least one nucleus in each case are separated from the body fluid and cultured for at least 24 hours, more particularly at least 2 days, more particularly at least 3 days, more particularly at least 4 days, more particularly at least 5 days, more particularly at least 6 days, more particularly at least 7 days, in suspension, i.e., with avoidance of cell adhesion to a substrate, to form spheroids. When cultured to form spheroids, the cells are cultured at least until they have formed spheroids by proliferation—optionally with the addition of at least one growth factor. Epithelial tumor cells are understood here to mean especially tumor cells bearing the epithelial cell adhesion molecule (EpCAM, CD326) or the corresponding animal molecule. In this connection, the cells can be, for example, carcinoma or sarcoma cells.

Cells containing no nucleus are generally erythrocytes possibly present in the body fluid. These may also be present in the separated cells. If intact erythrocytes are present in the body fluid, the cells containing at least one nucleus in each case can be separated from the intact erythrocytes, more particularly by lysing the intact erythrocytes. This can be done before, during or after separating the cells containing at least one nucleus in each case from the body fluid.

The culturing in suspension is a culturing procedure under conditions which do not allow adhesion to a substrate. Such culturing can be achieved by culturing without use of a cell culture vessel which is coated with collagen or promotes cell adhesion in some other way and/or moving a suspension containing the tumor cells at regular intervals or constantly. A cell culture vessel which promotes cell adhesion can, for example, consist of a plastic bearing charges on the surface. Cell adhesion can also be avoided when the cell culture vessel is a cell culture vessel coated with a silicone or a silane.

In contrast to the culturing procedure known from Lu et al., the culturing in suspension induces or allows a proliferation of a subpopulation of circulating epithelial tumor cells present in the body fluid which do not require adherence to a surface for proliferation.

According to Lu, J. et al., page 671, right-hand column, 2nd paragraph, nonadherent cells are removed after 12 hours and thus not cultured further. Circulating epithelial tumor cells which grow specifically adherently on a surface are thus cultured on a coated surface of a cell culture vessel and selected by the adhesion to said surface. However, the inventors of the present method have recognized that the circulating epithelial tumor cells comprise not only adherently growing cells, but also those cells which can proliferate clonally without adhesion. Furthermore, they have recognized that specifically the culturing of these nonadherently growing cells leads to cell clones, the cells of which are characteristic of the tumor disease and thus allow a good characterization of the tumor disease, even after removal of a primary tumor underlying the tumor disease. The tumor disease can be a carcinoma of the breast, prostate, lung, kidney, liver, pancreas or colon.

It has been found that crucial clinical significance is attached to the total circulating tumor cells for monitoring of an antitumor therapy, especially when detectable metastases have not yet formed. The response of the circulating tumor cells to a therapy correlates strongly with a relapse-free survival. From a large number of tumor cells released into the bloodstream from a tumor tissue of an epithelial tumor, only a fraction is, however, capable of forming metastases in secondary tissue.

The inventors of the method according to the invention have further recognized that the subpopulation of circulating tumor cells which can proliferate without adhesion are so-called tumor stem cells or tumor-initiating cells. They have also recognized that said cells grow in the form of spheroids, i.e., can form a spherical three-dimensional structure during proliferation. The culturing of epithelial tumor cells in suspension allows the formation of such spheroids and, as a result, detection of the presence of tumor stem cells as a subpopulation in the population of circulating tumor cells. In said spheroids, the stem cells form progenitor cells in different differentiation stages. It was previously unknown that circulating epithelial tumor cells comprise tumor stem cells which can be cultured in the form of spheroids. It is assumed that said tumor stem cells are of crucial importance for metastasis.

The body fluid can be lymph or blood, more particularly peripheral blood. The advantage of peripheral blood is good accessibility and ready availability.

In one embodiment of the method, the cells present in the body fluid and containing at least one nucleus in each case are separated from the body fluid without selection of certain of these cells, transferred to a cell culture medium and kept under cell culture conditions in a cell culture medium. In this connection, the cell culture conditions are generally those suitable for culturing epithelial cells. The cell culture medium generally contains an animal serum, such as, for example, fetal calf serum, L-glutamine, a growth stimulator, such as, for example, insulin, hydrocortisone, and a growth factor, such as, for example, EGF, in a culture medium, such as, for example, RPMI 1640, Dulbecco's Modified Eagle's Medium (DMEM) or a mixture of DMEM and RPMI 1640. The cell culture conditions generally comprise a temperature within the range of 35.5° C. to 37.5° C., more particularly a temperature within the range of 36.8° C. to 37.1° C., more particularly a temperature of 37° C., and an atmosphere containing 4.5% to 5.5% $CO_2$, more particularly 5% $CO_2$. Cell culture conditions suitable for epithelial cells and a cell culture medium suitable for epithelial cells are known to a person skilled in the art in the field of culturing mammalian cells, for example from Lu et al. Any necessary adaptations to the particular tumor cells, for instance in the selection of the underlying culture medium or the proportion of fetal calf serum, are within the scope of specialist skill and do not require any undue experimental burden.

Although the culturing, in suspension, of the cells separated from the body fluid without selection of certain cells causes a multiplicity of different cells, including leukocytes for example, to be transferred to the cell culture medium, only cells capable of proliferating in suspension do so. In this respect, the culturing brings about a specific multiplication of precisely these cells. Separating cells from the body fluid without selection of certain cells avoids losing the cells which can proliferate in suspension and frequently form only a small proportion of circulating epithelial tumor cells.

Fresh cell culture medium can be added to the cell culture medium repeatedly or regularly, for example every 5 days. Alternatively, the cells can be transferred to fresh cell culture medium repeatedly or regularly. To this end, the cells can be centrifuged carefully, i.e., at comparatively low rotational speeds, and resuspended in fresh cell culture medium.

In one embodiment of the method, tumor cells which have formed spheroids during culturing are separated from the cultured tumor cells, especially for further culturing, an analysis or a test for their sensitivity with respect to a therapeutic measure. The spheroids formed from tumor cells are hereinafter also referred to as tumor spheroids. Owing to the relatively large dimensions of the tumor spheroids in comparison with single cells, separation can be easily achieved, for example by centrifugation at a low rotational speed or by sedimentation or by sucking the tumor spheroids into a capillary under observation with a microscope.

The invention further provides for the use of the tumor cells cultured according to the invention and present in spheroids for the examination of a self-renewal capacity of the tumor cells present in the spheroids and/or of progenitor cells generated in the spheroids and/or for the testing of the sensitivity of the tumor cells in the spheroids with respect to a medicament or a therapeutic measure for treating a tumor disease underlying the occurrence of the circulating epithelial tumor cells in the human or animal, more particularly mammal. The inventors have recognized that the tumor cells present in the spheroids correspond to the cells which keep a tumor growth going in the human or animal, even after complete resection of a solid epithelial primary tumor, by forming a basis for the formation of metastases. Therefore, these tumor cells make it possible to characterize the tumor disease especially well. The self-renewal capacity and generation of progenitor cells also occurring in the spheroids is a special characteristic of tumor stem cells. Testing of the sensitivity of the cells forming the spheroids with respect to a medicament or a therapeutic measure for treating a tumor disease underlying the occurrence of the circulating epithelial tumor cells in the human or animal allows a good, completely new type of prediction concerning the efficiency of the medicament or the therapeutic measure in preventing metastasis formation in the tumor disease.

The therapeutic measure can be a physical measure, more particularly an irradiation or hyperthermia treatment, or a pharmaceutical measure, more particularly a chemotherapy, a hormone treatment or a treatment with antibodies. Furthermore, new and known medicaments can be tested for their efficacy on the tumor spheroids.

The tumor cells present in the spheroids can be fluorescently labeled using antibodies directed against the human epithelial antigen EpCAM (epithelial cell adhesion molecule) and then analyzed using an image analysis method, for example using laser radiation. To this end, it is not necessary to singularize the tumor cells. The antibodies allow a characterization of the cells as epithelial cells. In addition, the tumor cells present in the spheroids can be stained with a substance, more particularly propidium iodide, which is detectable by fluorescence and specifically or preferably stains dead cells. This allows the identification of dead cells, as frequently occur inside the spheroids for example. For image analysis, it is possible, for example, to use a laser scanning cytometer or a fluorescence microscope, more particularly one with an image acquisition unit/camera and analysis software, such as, for example, the Olympus SCAN® screening station.

In one embodiment of the use, labeling, measuring, and/or staining are carried out in the presence of a $Ca^{2+}$ chelator, more particularly EDTA or EGTA. The $Ca^{2+}$ chelator makes it possible to prevent clumping of the spheroids.

The invention further provides spheroid-forming tumor cells which have been cultured in accordance with a method according to the invention for the immunological treatment of a tumor disease in a human or animal, more particularly a mammal. To this end, the tumor cells present in the spheroids can, for example by means of radiation, be killed or at least treated such that they can no longer proliferate. Subsequently, the tumor cells can be suspended in an adjuvant and then administered, for example subcutaneously, to the human or animal. This triggers in the human or animal the formation of antibodies against the tumor cells which grow in the form of spheroids. The antibodies thereby formed can then also attack the other tumor cells in the human or animal and thus contribute to the regression of the tumor.

Figure 1B:
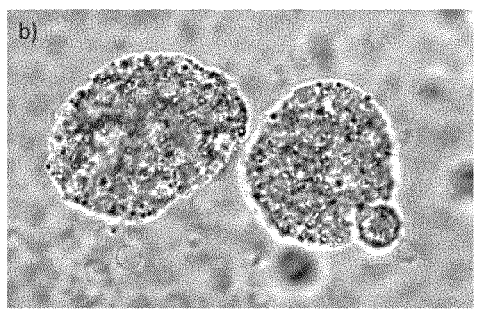
Figure 1C:
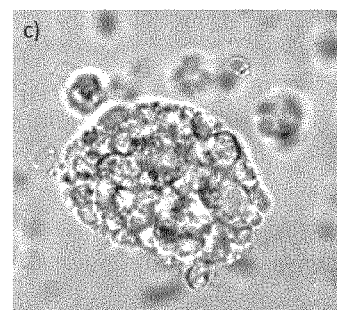
Figure 2:
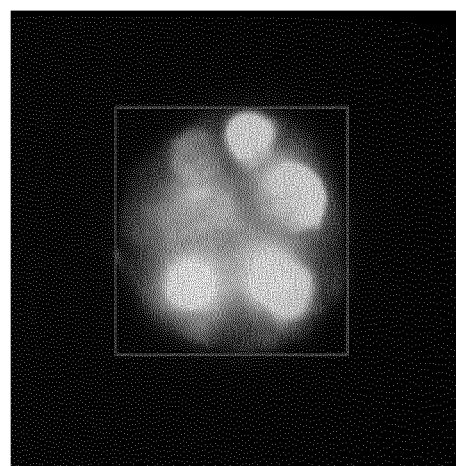

The invention will now be described in more detail on the basis of an exemplary embodiment and the figures. What are shown are:

FIG. 1a, b, c spheroids of tumor cells from peripheral blood from a patient suffering from colon carcinoma after culturing for 7 days (FIG. 1a), 14 days (FIG. 1b) and 21 days (FIG. 1c) and FIG. 2 a fluorescence microscopy image of a tumor spheroid fluorescently stained with antibodies and propidium iodide.

The methods described below were carried out using the following chemicals, reagents, buffers, solutions, antibodies, instruments and consumables and also the indicated medium:

Chemicals and reagents

| Chemicals and reagents | Company |
|---|---|
| Ammonium chloride ($NH_4Cl$) (155 mM) | Sigma-Aldrich, USA |
| Potassium bicarbonate ($KHCO_3$) (10 mM) | Sigma-Aldrich, USA |
| Ethylenediaminetetraacetate (EDTA) (0.5 M) | Sigma-Aldrich, USA |
| Dulbecco's Phosphate Buffered Saline (D-PBS) | GIBCO, USA |
| Flow-Check 770 Fluorospheres | Beckman Coulter, Ireland |
| Propidium iodide solution (1 mg) | Sigma-Aldrich, USA |
| RPMI 1640 (1X) 500 ml | Invitrogen GmbH, Germany |
| Hepes buffer solution (1 M) | Invitrogen GmbH, Germany |
| Penicillin/streptomycin (10000 U/10000 µg) | Invitrogen GmbH, Germany |
| L-Glutamine (200 mM) | Biochrom AG, Germany |
| Fetal bovine serum (FBS) | Invitrogen GmbH, Germany |
| Insulin (100 U/mL) | Sanofi-Aventis, USA |
| Hydrocortisone 100 mg | Pfizer, USA |
| EGF | Sigma-Aldrich, USA |

Buffers and solutions

| Buffers and solutions | Constituents | Amount |
|---|---|---|
| D-PBS | $CaCl_2$ | 0.901 mM |
| | $MgCl_2\text{-}6H_2O$ | 0.493 mM |
| | KCl | 2.67 mM |
| | $KH_2PO_4$ | 1.47 mM |
| | NaCl | 137.93 mM |
| | $Na_2HPO_4\text{-}7H_2O$ | 8.06 mM |
| D-PBS-EDTA | D-PBS | 500 ml |
| | EDTA | 2 ml |
| Erythrocyte lysis buffer | $NH_4Cl$ | 8.3 g |
| (dissolve in 1 L of distilled water) | $KHCO_3$ | 1 g |
| | EDTA | 2 ml |
| Propidium iodide solution (in 1 ml of distilled water) | PI | 3.5 µl |

Antibodies

| Antibodies | Company | Article number |
|---|---|---|
| CD 326 (EpCAM) conjugated with fluorescein isothiocyanate (FITC) | Miltenyi Biotec GmbH, Germany | 130-080-301 |

Instruments

| Instruments | Company |
|---|---|
| Centrifuge 5810 R | Eppendorf, Germany |
| Laser scanning microscope iCys ™ | CompuCyte Corporation, USA |
| Vortexer | Bender und Hobein GmbH, Germany |

Consumables

| Consumables | Company |
|---|---|
| 15 ml Falcon tubes | Labor Schubert, Germany |
| 1.5 ml Eppendorf tubes | Labor Schubert, Germany |
| Micropipettes | Eppendorf, Germany |
| Disposable Pasteur pipettes, graduated (3.2 ml) | ROTH, Germany |

-continued

Consumables

| Consumables | Company |
|---|---|
| Microtiter plates (MTP) with glass base | Greiner bio-one, Germany |
| Culture flasks (25 $cm^2$, 65 ml) | neoLab, Germany |

Composition of the medium

| Chemicals | Final concentration |
|---|---|
| A culture medium, preferably RPMI 1640 | |
| A serum additive, preferably fetal calf serum | 5% |
| L-Glutamine | 4 mM |
| Hepes | 15 mM |
| Growth stimulator, | 5 µg/ml |

-continued

| Composition of the medium | |
|---|---|
| Chemicals | Final concentration |
| preferably insulin | |
| Hydrocortisone | 0.5 µg/ml |
| Antibiotics, preferably penicillin/streptomycin | 100 U/ml; 100 µg/ml |
| Growth factors, preferably EGF | 40 ng/ml |

Blood samples were collected from the peripheral vein in 2-7 ml tubes containing EDTA as anticoagulant. The viability of the circulating epithelial tumor cells was on average 95%.

In a sample tube, 1 ml of the particular blood sample was topped up to a total volume of 15 ml using the erythrocyte lysis buffer and incubated in the refrigerator for 15 min at a temperature of 4° C. Next, the sample was centrifuged at 2000 rpm for 7 min and at a temperature of 18° C. The supernatant was then decanted. Thereafter, the pellet was resuspended with 2 ml of medium and transferred to a culture flask into an initially charged 3 ml of medium (depending on the leukocyte count: 5 ml of medium per 10 000 leukocytes). This was incubated for 21 days at 5% $CO_2$ and 37° C. Every 5 days, 2 ml of fresh medium were added. Every 7 days, i.e., on the 7th, 14th, 21st and 28th day, the tumor spheroids were examined under the microscope. For the analysis, the tumor spheroids were collected by means of a gentle centrifugation and then the pellet was resuspended with 500 µl of D-PBS-EDTA. 50 µl of this mixture were then transferred to a 1.5 ml Eppendorf tube. Thereafter, 5 µl of a (FITC)-monoclonal antibody against the human epithelial antigen (EpCAM) were pipetted thereinto. This was followed by another 15-minute cooling at 4° C. Lastly, 430 µl of D-PBS-EDTA were added and the samples, now completed, were stored overnight in the refrigerator at 4° C.

On the following day, 100 µl of cell suspension of the sample to be measured and 5 µl of propidium iodide (PI) were pipetted in each case into a well of an ELISA plate. The plate was then covered and allowed to rest for about 20 min so that the cells could sediment on the base. Subsequently, the cells were measured using the laser scanning cytometer and the measurement results were evaluated.

What were obtained were nonadherent, three-dimensional spheroids, which are typical of the presence of tumor stem cells. FIG. 1a shows the spheroids after 7 days of culturing, FIG. 1b shows them after 14 days of culturing, and FIG. 1c shows them after 21 days of culturing. FIG. 2 shows a red-stained necrotic tumor cell in the middle of a tumor spheroid cell aggregate. The death of this tumor cell may possibly be due to a lack of diffusion of growth factors through the tight cell packing surrounding said cell.

It was possible to culture a subpopulation of the circulating epithelial tumor cells which forms spheroids and has a high capacity for proliferation.

The invention claimed is:

1. A method for culturing circulating epithelial tumor cells from a body fluid from a human or animal affected by an epithelial tumor, comprising:
   (i) separating cells present in the body fluid and containing at least one nucleus in each case from the body fluid without selection of certain of these cells;
   (ii) transferring said separated cells to a cell culture medium; and
   (iii) culturing said transferred separated cells under cell culture conditions in said cell culture medium containing at least an animal serum, a growth stimulator and one growth factor, wherein the growth stimulator is insulin and hydrocortisone and wherein the growth factor is Epidermal growth factor, and wherein the cells are cultured for at least 24 hours in suspension at least until a subpopulation of tumor cells, which does not require adherence to a surface for proliferation, has formed spheroids by proliferation, and wherein tumor cells which have formed the spheroids during culturing are separated from the cultured tumor cells by separating the spheroids formed during culture.

2. The method as claimed in claim 1, wherein the body fluid is lymph or blood.

3. The method as claimed in claim 1, wherein the body fluid contains intact erythrocytes and the cells containing at least one nucleus in each case are separated from the intact erythrocytes.

4. The method as claimed in claim 1, wherein the cell culture conditions comprise a temperature within the range of 35.5° C. to 37.5° C., and an atmosphere containing 4.5% to 5.5% $CO_2$.

5. The method as claimed in claim 1, wherein fresh cell culture medium is added to the cell culture medium repeatedly or regularly, or wherein the cells are transferred to fresh cell culture medium repeatedly or regularly.

6. The method as claimed in claim 2, wherein the body fluid is peripheral blood.

7. The method as claimed in claim 3, wherein the cells containing at least one nucleus in each case are separated from the intact erythrocytes by lysing the intact erythrocytes.

8. The method as claimed in claim 4, wherein the temperature is within the range of 36.8° C. to 37.1° C.

9. The method as claimed in claim 4, wherein the temperature is 37° C. and the atmosphere contains 5% $CO_2$.

* * * * *